(12) United States Patent
Chiacchio et al.

(10) Patent No.: US 6,762,327 B2
(45) Date of Patent: Jul. 13, 2004

(54) SELECTIVE OXIDATION PROCESS WITH ENHANCED SAFETY

(75) Inventors: Ugo Chiacchio, Acireale (IT); Antonio Rescifina, Acicatena (IT); Giuseppe Miraglia, Catania (IT); Mariangela Magnano, San Gregorio di Catania (IT); Paola Di Raimondo, San Gregorio di Catania (IT)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/406,394

(22) Filed: Apr. 3, 2003

(65) Prior Publication Data

US 2003/0204064 A1 Oct. 30, 2003

Related U.S. Application Data

(60) Provisional application No. 60/376,318, filed on Apr. 29, 2002.

(51) Int. Cl.$^7$ .......................... C07C 45/29; C07C 53/00; C07D 307/00
(52) U.S. Cl. ................ 568/354; 568/355; 568/361; 568/446; 562/887; 549/302; 549/305; 549/307
(58) Field of Search ................ 568/354, 355, 568/361, 446; 562/887; 549/302, 305, 307

(56) References Cited

U.S. PATENT DOCUMENTS

| | | |
|---|---|---|
| 3,505,354 A | 4/1970 | Doebel et al. |
| 4,894,386 A | 1/1990 | Brown et al. |
| 4,988,824 A | 1/1991 | Maulding et al. |
| 5,420,289 A | 5/1995 | Musser et al. |

OTHER PUBLICATIONS

Dess et al. A Useful 12–1–5 Triacetoxyperiodinane (the Dess–Martin Periodinane) for the Selective Oxidation of Primary or Secondary Alcohols and a Variety of Related 12–1–5 Species. □□Journal of the American Chemical Society, 1991, vol. 113, pp. 7277–7287.*
Barrett et al. Dess–Martin Periodinane Oxidation of Alcohols in the Presence of Stabilized Phosphorus Ylides: A Convenient method for the Homologation of Alcohols Via Unstable Aldehydes. □□Journal of Organic Chemistry, 1997, vol. 62, pp. 9376–9378.*
Sergio De Munari, et al., Journal of Organic Chemistry, 61, 1996, pp. 9272–9279.
Robert E. Ireland, et al., Journal of Organic Chemistry, 58, 1993, pp. 2899.
D.B. Dess, et al., Journal of Organic Chemistry, 48, 1983, pp. 4155–4156.
J.B. Plumb, et al., Chemical & Engineering News, Jul. 16, 1990, p. 3.

* cited by examiner

*Primary Examiner*—Shailendra Kumar
*Assistant Examiner*—Sikarl A. Witherspoon
(74) *Attorney, Agent, or Firm*—John F. Levis

(57) ABSTRACT

A safe and effective process for the oxidation of a primary or secondary alcohol to the corresponding aldehyde or ketone via the reaction of said alcohol with an anhydride solution of a 1,1,1-tri($C_2$–$C_4$ alkanoyloxy-1,1-dihydro-1,2-benziodoxol-3(1H)-one, and a composition useful in this process.

16 Claims, No Drawings

SELECTIVE OXIDATION PROCESS WITH ENHANCED SAFETY

This application claims the benefit of Provisional Application No. 60/376,318, filed Apr. 29, 2002.

BACKGROUND OF THE INVENTION

Hypervalent iodine (V) compounds are known to be useful oxidizing agents for the conversion of primary and secondary alcohols to their corresponding aldehydes and ketones, e.g. De Munari, S. et al, Journal of Organic Chemistry, 1996, 61, pp. 9272–9279. Dess-Martin periodinane (DMP), 1,1,1-triacetoxy-1,1-dihydro-1,2-benziodoxol-3(1H)-one, is often the reagent of choice for the oxidation of primary and secondary alcohols due to mild reaction conditions (room temperature and either slightly acidic or neutral pH) which are especially suitable for substrates which contain sensitive functional groups. However, DMP explodes violently upon heating under confinement (Chemical & Engineering News, Jul. 16, 1990, p. 3). The hazardous explosive properties of DMP make its use on a manufacturing scale prohibitively dangerous.

Therefore, it is an object of this invention to provide a selective and safe oxidation process for the conversion of a primary or secondary alcohol to the corresponding aldehyde or ketone.

It is another object of this invention to provide an oxidation process which affords high product yields.

It is also an object of this invention to provide a composition useful in the process of this invention.

It is a feature of this invention that the oxidizing agent is used in situ, thereby eliminating the need for additional separation or isolation steps.

These and other objects and features of the invention will become more apparent from the detailed description set forth herein below.

SUMMARY OF THE INVENTION

The present invention provides a safe and effective process for the selective oxidation of a primary or secondary alcohol to the corresponding aldehyde or ketone which process reacting said alcohol with a solution containing an anhydride of the formula $(RCO)_2O$ and a trialkanoyl periodinane compound of formula I

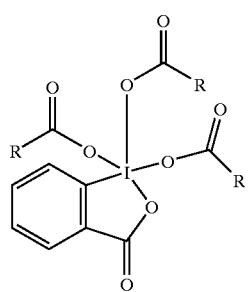

(I)

wherein R is $C_2$–$C_4$ alkyl. Preferably, R is ethyl or n-propyl.

The present invention also provides a composition useful in the process of the invention, which composition comprises a solution of an anhydride of the formula $(RCO)_2O$ and a trialkanoyl periodinane compound of formula I dissolved in a suitable solvent, e.g., an aromatic hydrocarbon such as toluene.

DETAILED DESCRIPTION OF THE INVENTION

Dess-Martin periodinane (DMP), 1,1,1-triacetoxy-1,1-dihydro-1,2-benziodoxol-3(1H)-one, is an organoiodine compound which is useful for the facile and efficient oxidation of primary alcohols to aldehydes and secondary alcohols to ketones (Journal of Organic Chemistry, 1983, 48, 4155–4156). Although the use of DMP avoids some common difficulties encountered in using other procedures for oxidizing alcohols such as long reaction times, difficult workup procedures or the need to use a large excess of the oxidizing agent, the propensity of DMP to explode violently on heating under confinement prohibits its use on a commercial manufacturing scale.

Surprisingly, it has now been found that an anhydride solution of a trialkanoyl periodinane compound of formula I may be used to selectively oxidize a primary or secondary alcohol to the corresponding aldehyde or ketone under mild reaction conditions, with high product yield and without the hazardous chemical properties (heat/shock sensitive) associated with DMP.

Although the process of the invention is suitable for the oxidation of any primary or secondary alcohol, it is particularly suitable for substrates which contain sensitive functional groups. For example, macrolide compounds, such as 5-{[(p-nitrophenyl)-carbonyl]oxy}-F28249alpha (5-pnb-F28249alpha), may be oxidized to their corresponding ketones via the inventive process on a manufacturing scale with significantly enhanced product yield. In the case of 5-pnb-F28249alpha, the 23-keto product may then be converted to the potent endectocidal agent, moxidectin. The process is described in U.S. Pat. No. 4,988,824. The oxidation step of the process is shown in flow diagram I.

FLOW DIAGRAM I

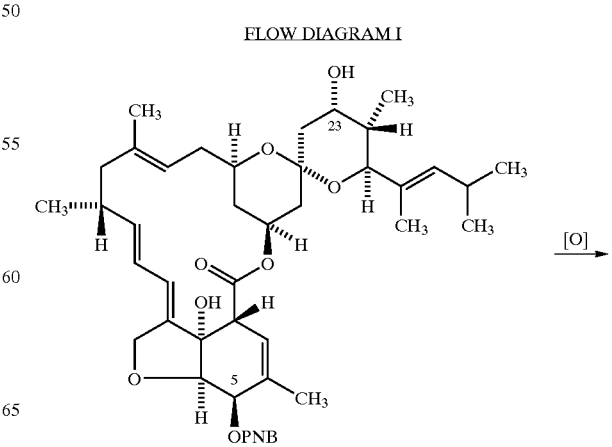

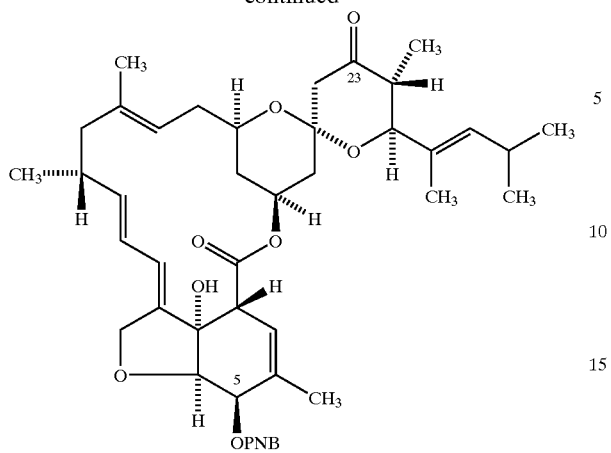

In a preferred embodiment of this invention, a solution containing a (RCO)₂O and a trialkanoyl periodinane compound of formula I contains about 2 mol % to 15 mol %, preferably about 4 mol %, to 6 mol %, more preferably about 5 mol % of the formula I compound, is admixed with a primary or secondary alcohol, optionally in the presence of a solvent at room temperature until oxidation is complete. Reaction times for the process of the invention may vary according to the stereochemical character of the alcohol, the concentration of the alcohol, or the like; in general, reaction times of one hour or less are sufficient to complete the oxidation. For optimum product yield, at least 1.0, preferably about 1.0–1.5, equivalents of the formula I compound is suitable for use in the inventive process.

In a highly preferred embodiment of the invention, the anhydride and the trialkanoyl periodinane are dissolved in toluene, although other suitable solvents may be used, particularly other aromatic hydrocarbons, preferably containing approximately 6–12 carbon atoms. A solvent is suitable if it dissolves the anhydride and the trialkanoyl periodinane compound, and does not adversely affect or interfere with the oxidation reaction. Those skilled in the art will be able to readily identify suitable solvents without undue experimentation.

It is highly preferred that the R group in the anhydride and the trialkanoyl periodinane compound is ethyl or n-propyl.

The 1,1,1-trialkanoyl periodinane of formula I may be prepared by conversion of 1-hydroxy-1,2-benziodoxol-3(1H)one 1-oxide (formula II) according to the following reaction, in which PTSA represents p-toluenesulfonic acid:

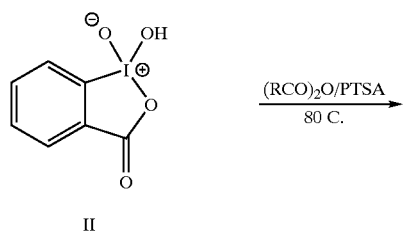

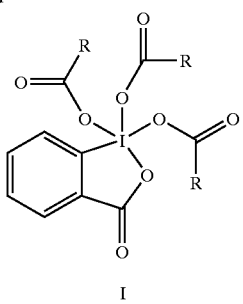

The compound of formula I does not need to be isolated, but may be used to oxidize alcohols in the anhydride solution. This avoids the extra work and expense of isolating the compound, as well as any concerns about instability of the compound in its solid state.

In order to facilitate a further understanding of the invention, the following examples are presented primarily for the purpose of illustrating more specific details thereof. The invention is not to be limited thereby except as defined in the claims.

Unless otherwise noted, all parts are parts by weight. The terms HPLC and HNMR designate high performance chromatography and proton nuclear magnetic resonance, respectively.

EXAMPLE 1

Preparation of 1,1,1-Tripropionyloxy-1,1-dihydro-1,2-benziodoxol-3(1H)-one

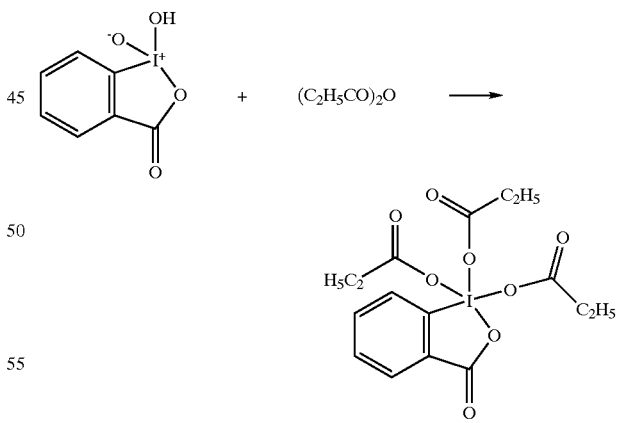

A stirred mixture of 1-hydroxy-1,2-benziodoxol-3(1H)-one 1-oxide (9.33 g, 0.033 mol), propionic anhydride (51.3 g, 0.396 mol) and p-toluenesulfonic acid (0.045 g) is heated under nitrogen at 80° C. for 5 h, cooled to room temperature and concentrated in vacuo. The resultant residue is washed with ether and air-dried to give the title product as a white solid, 13.84 g, identified by HNMR analysis.

EXAMPLE 2

Preparation of 1,1,1-tri-n-butanoyloxy-1,1-dihydro-1,2-benziodoxol-3(1H)-one

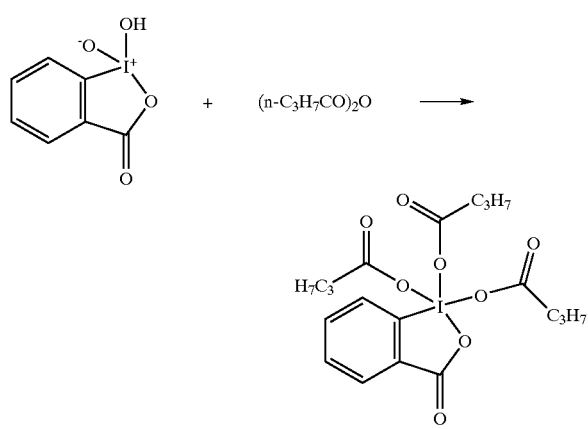

A stirred mixture of 1-hydroxy-1,2-benziodoxol-3(1H)-one 1-oxide (9.33 g, 0.033 mol), butyric anhydride (62.65 g, 0.396 mol) and p-toluenesulfonic acid (0.045 g) is heated under nitrogen at 80° C. for 5 h and cooled to room temperature. The resultant solution of the title product in butyric anhydride is used as is in Example 3.

EXAMPLE 3

The Selective Oxidation of a Primary or Secondary Alcohol to the Corresponding Aldehyde or Ketone.

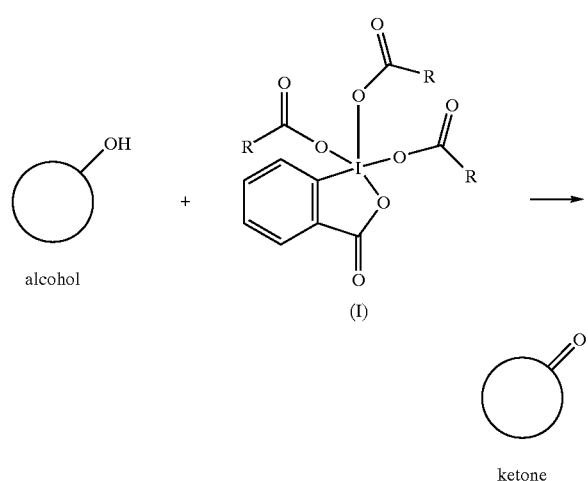

A mixture of the alcohol, e.g., cyclohexanol (14.3 mmol) or 5-{[(p-nitrophenyl)carbonyl]oxy}-F28249alpha (13.1 mmol), and an anhydride solution of a 1,1,1-trialkanoyloxy-1,1-dihydro-1,2-benziodoxol-3(1H)-one (15.7 mmol) as described in Example 2 is stirred under nitrogen at room temperature. The reaction progress is monitored by HPLC. When the conversion is complete, the reaction is quenched with an aqueous solution of $NaHCO_3/Na_2S_2O_3$ and stirred for 10 minutes. The phases are separated; the organic phase is filtered and the product is identified by HPLC. The process conditions and product yields are shown in Table I.

TABLE I

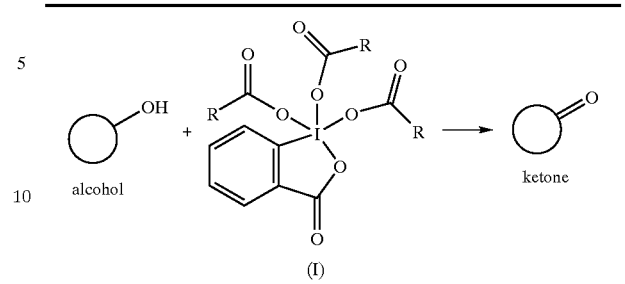

| Alcohol | R | Equv. Of (I) | Time h | % Yield |
| --- | --- | --- | --- | --- |
| Cyclohexanol | $C_2H_5$ | 1.1 | 0.5 | 95 |
| Cyclohexanol | $C_3H_7$ | 1.1 | 0.5 | 95 |
| n-Octanol | $C_2H_5$ | 1.1 | 0.5 | 97 |
| n-Octanol | $C_3H_7$ | 1.1 | 0.5 | 97 |
| Cyclooctanol | $C_2H_5$ | 1.1 | 0.5 | 100 |
| Cyclooctanol | $C_3H_7$ | 1.1 | 0.5 | 100 |
| Benzyl alcohol | $C_2H_5$ | 1.1 | 0.5 | 94 |
| Benzyl alcohol | $C_3H_7$ | 1.1 | 0.5 | 94 |
| 2,5-Dimethoxybenzyl alcohol | $C_2H_5$ | 1.1 | 0.3 | 96 |
| 2,5-Dimethoxybenzyl alcohol | $C_3H_7$ | 1.1 | 0.3 | 96 |
| 3,4,5-Trimethoxy-benzyl alcohol | $C_2H_5$ | 1.1 | 0.3 | 95 |
| 3,4,5-Trimethoxy-benzyl alcohol | $C_2H_5$ | 1.1 | 0.3 | 95 |
| 5-{[(p-Nitrophenyl)-carbonyl]oxy}-F28249 alpha | $C_2H_5$ | 1.2 | 0.5 | 80 |
| 5-{[(p-Nitrophenyl)-carbonyl]oxy}-F28249 alpha | $C_3H_7$ | 1.2 | 0.5 | 88 |

What is claimed is:

1. A process for the selective oxidation of a primary or secondary alcohol to the corresponding aldehyde or ketone which comprises reacting said alcohol with a solution containing an anhydride of the formula $(RCO)_2O$ and a trialkanoyl periodinane compound of formula I

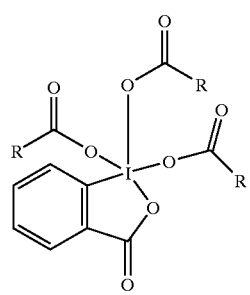

(I)

wherein R is $C_2$–$C_4$ alkyl.

2. The process according to claim 1 wherein R is ethyl or n-propyl.

3. The process according to claim 2 wherein said alcohol is 5-{[(p-nitrophenyl)carbonyl]oxy}-F28249alpha, and the oxidation produces the 23-keto derivative of said alcohol.

4. The process according to claim 3 further comprising the conversion of the 23-keto derivative to moxidectin.

5. The process according to claim 2 wherein said alcohol is selected from the group consisting of: cyclohexanol;

n-octanol; cyclooctanol; benzyl alcohol; 2,5-dimethoxybenzyl alcohol; and 3,4,5-trimethoxybenzyl alcohol.

6. A composition which comprises a solution of an anhydride of the formula $(RCO)_2O$ and a trialkanoyl periodinane compound of formula I

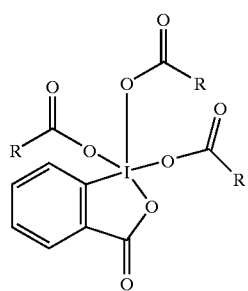

(I)

wherein R is $C_2$–$C_4$ alkyl, dissolved in a suitable solvent.

7. The composition according to claim 6 wherein R is ethyl or n-propyl.

8. The composition according to claim 6 wherein the formula I compound is present in the amount of about 2 mol % to 15 mol %.

9. The composition according to claim 7 wherein the formula I compound is present in the amount of about 4 mol % to 6 mol %.

10. The composition according to claim 7 wherein said solvent is toluene.

11. The composition according to claim 6 wherein said solvent is toluene.

12. A process for the selective oxidation of a primary or secondary alcohol to the corresponding aldehyde or ketone which comprises reacting said alcohol with a solution containing an anhydride of the formula $(RCO)_2O$ and a trialkanoyl periodinane compound of formula I.

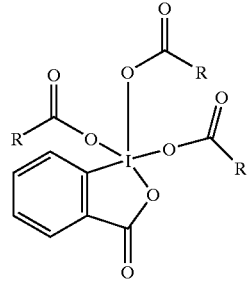

(I)

wherein R is $C_2$–$C_4$ alkyl, dissolved in a suitable solvent.

13. The process according to claim 12 wherein the formula I compound is present in the amount of about 2 mol % to 15 mol %.

14. The process according to claim 12 wherein the formula I compound is present in the amount of about 4 mol % to 6 mol %.

15. The process according to claim 14 wherein the solvent is toluene.

16. The process according to claim 12 wherein the solvent is toluene.

* * * * *